US006946457B2

(12) United States Patent
DeBellis et al.

(10) Patent No.: US 6,946,457 B2
(45) Date of Patent: Sep. 20, 2005

(54) METHODS OF TREATING SICKLE CELL DISEASE

(75) Inventors: Robert H. DeBellis, Englewood, NJ (US); Bernard F. Erlanger, Whitestone, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 76 days.

(21) Appl. No.: 09/828,413

(22) Filed: Apr. 6, 2001

(65) Prior Publication Data

US 2004/0204430 A1 Oct. 14, 2004

(51) Int. Cl.$^7$ ............................................. A61K 31/545
(52) U.S. Cl. .................................. 514/210.01; 514/815
(58) Field of Search ............................ 514/210, 210.01

(56) References Cited

U.S. PATENT DOCUMENTS 5,939,456 A * 8/1999 Perrine ........................ 514/554

OTHER PUBLICATIONS

Lori et al., "Hydroxyurea as an inhibitor of human immunodeficiency virus–type 1 replicaton", Science 266 (5186) : 801–5 (1994).*
Lawson et al., "Acute Renal Insufficiency Due to Oral Acyclovir in a Man With Sickle Cell Trait", Southern Medical Journal 92 (11) : 10943–4 (1999).*
Chinowsky, "Thrombotic Thrombocytopenic Purpura Associated With Sickle Cell–Hemoglobin C Disease", Southern Medical Journal 87 (11) : 1168–71 (1994).*
De Castro, "Prevalence of Hepatitis C in Adults with Sickle Cell Disease", Blood 96 (11) : 15b (2000).*
Adachi, K. et al., (1980) "Nucleation–Controlled Aggregation Of Deoxyhemoglobin S Participation Of Hemoglobin A In The Aggregation Of Deoxyhemoglobin S In Concentrated Phosphate Buffer" *J. Biol. Chem.* 255: 3092–3099 (Exhibit 1).
Ballas, S.K. et al., (1989) "Effect Of Hydroxyurea On The Rheological Properties Of Sickle Erythrocytes In Vivo" *Am. J. Hematol.* 32: 104–111 (Exhibit 2).
Bunn, H.F. (1997) "Pathogenesis And Treatment Of Sickle Cell Disease" *N. Engl. J. Med.* 337: 762–769 (Exhibit 3).
Charache, S. et al., (1987) "Hydroxyurea–Induced Augmentation Of Fetal Hemoglobin Production In Patients With Sickle Cell Anemia" *Blood* 69: 109–116 (Exhibit 4).
Charache, S. et al., (1995) "Effect Of Hydroxyurea On The Frequency Of Painful Crises In Sickle Cell Anemia" *N. Engl. J. Med.* 332: 1317–1322 (Exhibit 5).
Charache, S., and C.L. Conley (1964) "Rate Of Sickling Of Red Cells During Deoxygenation Of Blood From Persons With Various Sickling Disorders" *Blood* 24: 25–48 (Exhibit 6).
Dover, G.J. et al., (1986) "Hydroxyurea Induction Of Hemoglobin F Production In Sickle Cell Disease; Relationship Between Cytotoxicity And F Cell Production" *Blood* 67: 735–738 (Exhibit 7).
Ferster, A. et al., (1996) "Hydroxyurea For Treatment Of Severe Sickle Cell Anemia: A Pediatric Clinical Trial" *Blood* 88: 1960–1964 (Exhibit 8).
Gillette, P.N. et al., (1974) "Sodium Cyanate As A Potential Treatment For Sickle Cell Disease" *N. Eng. J. Med.* 290: 654–660 (Exhibit 9).
Goldberg, M.A. et al., (1990) "Treatment Of Sickle Cell Anemia With Hydroxyurea And Erythropoietin" *N. Engl. J. Med.* 323: 366–372 (Exhibit 10).
Hahn, E.V., and E.B. Gillespie (1927) "Sickle Cell Anemia: Report Of A Case Greatly Improved By Splenectomy: Experimental Studies Of Sickle Cell Formation" *Arch. Intern. Med.* 39: 233–254 (Exhibit 11).
Huisman, T.H.J. and A.M. Dozy (1965) "Studies On The Heterogeneity Of Hemoglobin. IX. The Use Of Tris (Hydroxymethyl) Aminomethane–HCl Buffers In The Anion–Exchange Of Chromatography Hemoglobins" *J. Chromatog.* 19: 160–169 (Exhibit 12).
Orringer, E.P. et al., (1991) "Effects Of Hydroxyurea On Hemoglobin F And Water Content In The Red Blood Cells Of Dogs And Of Patients With Sickle Cell Anemia" *Blood* 78: 212–216 (Exhibit 13).
Pauling, L. et al., (1949) "Sickle Cell Anemia, A Molecular Disease" *Science* 110: 543–548 (Exhibit 14).
Steinberg, M.H. (1999) "Management Of Sickle Cell Disease" *N. Engl. J. Med.* 340: 1021–1030 (Exhibit 15).
Rogers, G.P. et al., (1990) "Hemotologic Responses Of Patients With Sickle Cell Disease To Treatment With Hydroxyurea" *N. Engl. J. Med.* 322: 1037–1045 (Exhibit 16).

* cited by examiner

Primary Examiner—Sandra E. Saucier
(74) Attorney, Agent, or Firm—John P. White, Esq.; Cooper & Dunham LLP

(57) ABSTRACT

This invention provides a method of treating a subject afflicted with sickle cell disease which comprises administering to the subject an amount of an antiviral agent effective to inhibit sickling of a cell in the subject, so as to thereby treat the subject afflicted with sickle cell disease. This invention also provides a method of inhibiting polymerization of hemoglobin which comprises contacting the hemoglobin with an amount of an antiviral agent effective to inhibit polymerization of the hemoglobin, so as to thereby inhibit polymerization of the hemoglobin. This invention further provides a method of inhibiting sickling of a cell which comprises contacting the cell with an amount of an antiviral agent effective to inhibit polymerization of hemoglobin in the cell, so as to thereby inhibit sickling of the cell.

5 Claims, 7 Drawing Sheets

METHODS OF TREATING SICKLE CELL DISEASE

Throughout this application, various references are referred to within parentheses. Disclosures of these publications in their entireties are hereby incorporated by reference into this application to more fully describe the state of the art to which this invention pertains. Full bibliographic citation for these references may be found immediately preceding the claims.

BACKGROUND OF THE INVENTION

Despite considerable knowledge regarding the etiology of sickle cell disease, effective treatment has been elusive. Modalities for therapy have largely been directed at symptomatology. This disease is a major cause of illness in black populations throughout the world; it is estimated that 1 in 600 black individuals suffer from this disorder and that 8% are heterozygous carriers of the trait. Moreover, an equal number of individuals suffer from sickle cell equivalents (sickle cell-hemoglobin C disease and sickle cell-β-thalassemia) (1).

Since the discovery of the etiology of sickle cell disease in 1949 by Pauling and his colleagues (2), a vast literature has grown in the fields of biochemistry, molecular biology and genetics regarding the mechanisms involved in the aggregation or polymerization of hemoglobin S ("HbS"), the sickling of intact erythrocytes and the inhibition of sickling by other hemoglobins (see review by Bunn) (3).

Despite the voluminous literature, little progress has been made in the treatment of this disabling disorder. The ideal treatment would involve replacement of the gene for $β^S$ production with an innocuous substitution. Many laboratories are pursuing this goal, to date none successfully (4). An alternative treatment would involve an oral, readily absorbed, non-toxic agent, capable of entering erythrocytes where it would inhibit gelation of HbS and ultimate sickling of the cells. To date no such agents have been identified.

At present, perhaps the drug used most frequently in the treatment of sickle cell disease is hydroxyurea, a commonly used chemotherapeutic agent (5). Treatment with hydroxyurea depends primarily on induction of the biosynthesis of intracellular hemoglobin F (HbF) (6–11), a hemoglobin known to be effective in inhibiting sickling both in vitro and in vivo. Clinical trials with hydroxyurea have demonstrated a reduction in frequency and severity of painful crises and in transfusion requirements (10–12). Despite the benefits of hydroxyurea therapy, there is concern regarding the consequences of long term use of an anti-neoplastic agent, and treatment is far from optimal.

The present discovery relates to uses of antiviral agents such as acyclovir and valacyclovir to inhibit the aggregation of HbS and the sickling of erythrocytes taken from patients with sickle cell disease both in vitro and in vivo. The low toxicity of the agents at the relatively high concentrations used to treat herpetic infections makes them good agents for the treatment of sickle cell disease.

SUMMARY OF THE INVENTION

This invention provides a method of treating a subject afflicted with sickle cell disease which comprises administering to the subject an amount of an antiviral agent effective to inhibit sickling of a cell in the subject, so as to thereby treat the subject afflicted with sickle cell disease.

This invention provides a method of inhibiting polymerization of hemoglobin which comprises contacting the hemoglobin with an amount of an antiviral agent effective to inhibit polymerization of the hemoglobin, so as to thereby inhibit polymerization of the hemoglobin.

This invention provides a method of inhibiting sickling of a cell which comprises contacting the cell with an amount of an antiviral agent effective to inhibit polymerization of hemoglobin in the cell, so as to thereby inhibit sickling of the cell.

This invention provides a method of determining whether an antiviral agent is capable of treating a subject afflicted with sickle cell disease which comprises: (a) obtaining a suitable sample of cells from a subject afflicted with sickle cell disease; (b) subjecting the sample to conditions such that the cells in the sample sickle; and (c) comparing the amount of sickling of the cells in the presence of the antiviral agent with the amount of sickling of the cells in the absence of the antiviral agent, wherein an absence of sickling or a reduction in the amount of sickling in the cells in the presence of the antiviral agent compared with the amount of sickling of the cells in the absence of the antiviral agent indicates that the antiviral agent is capable of treating a subject afflicted with sickle cell disease.

This invention provides a method of determining whether an antiviral agent is capable of inhibiting sickling of a cell which comprises: (a) obtaining a suitable sample of cells from a subject afflicted with sickle cell disease; (b) subjecting the sample to conditions such that the cells in the sample sickle; and (c) comparing the amount of sickling of the cells in the presence of the antiviral agent with the amount of sickling of the cells in the absence of the antiviral agent, wherein an absence of sickling or a reduction in the amount of sickling in the cells in the presence of the antiviral agent compared with the amount of sickling of the cells in the absence of the antiviral agent indicates that the antiviral agent is capable of inhibiting sickling of the cell.

This invention provides a method of determining whether an antiviral agent is capable of inhibiting polymerization of hemoglobin which comprises: (a) obtaining a suitable sample of hemoglobin from a subject afflicted with sickle cell disease; (b) subjecting the sample to conditions such that the hemoglobin polymerizes; and (c) comparing the amount of turbidity of the sample in the presence of the antiviral agent with the amount of turbidity of the sample in the absence of the antiviral agent, wherein an absence or reduction in the amount of turbidity in the sample in the presence of the antiviral agent compared with the amount of turbidity in the sample in the absence of the antiviral agent indicates that the antiviral agent is capable of inhibiting polymerization of hemoglobin. cells.

Figure 1:
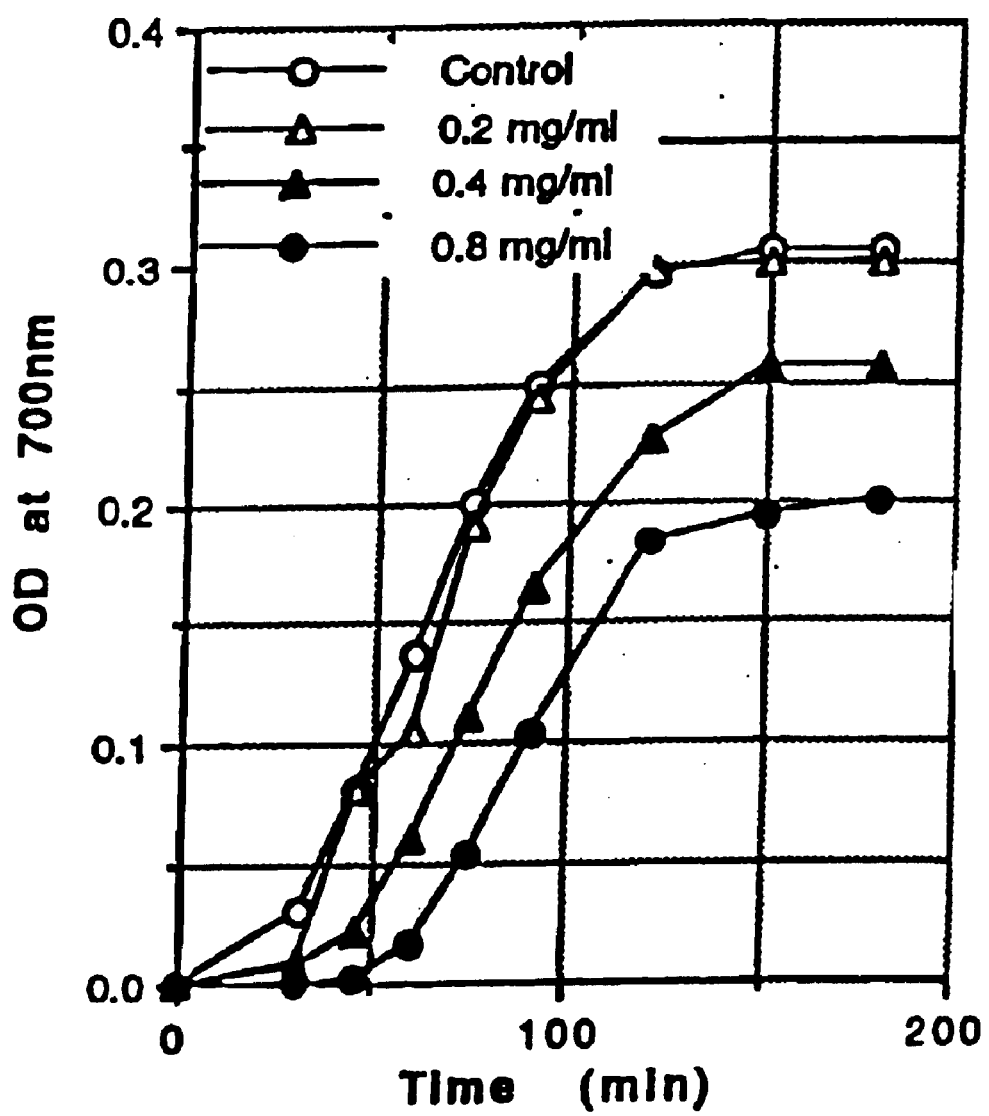
FIG. 1

Effect of various concentrations of acyclovir on the aggregation of deoxygenated hemoglobin S.

FIG. 2

(A) Sickling of deoxygenated erythrocytes in the absence of added reagents, i.e. the control. (B) Sickling of deoxygenated erythrocytes in the presence of 0.2 mg/ml of acyclovir. (C) Sickling of deoxygenated erythrocytes in the presence of 0.3 mg/ml of acyclovir. (D) Sickling of deoxygenated erythrocytes in the presence of 0.4 mg/ml of acyclovir. (E) Erythrocytes from the same patient under aerobic conditions.

FIG. 3

Effect of compounds, including acyclovir and valacyclovir, on the aggregation of deoxygenated hemoglobin S. (Legend: -o- control; -●- valacyclovir; -x-acyclovir; -Δ- glycophage X; -▲- Diphen).

DETAILED DESCRIPTION OF THE INVENTION

This invention provides a method of treating a subject afflicted with sickle cell disease which comprises administering to the subject an amount of an antiviral agent effective to inhibit sickling of a cell in the subject, so as to thereby treat the subject afflicted with sickle cell disease.

As used herein, "treating" means either slowing, stopping or reversing the progression of the sickling of a cell. In the preferred embodiment, "treating" means reversing the progression to the point of eliminating the presence of sickled cells. As used herein, "treating" also means the reduction in the amount of polymerization of hemoglobin or the amelioration of symptoms associated with sickle cell disease.

As used herein, "afflicted with sickle cell disease" means that the subject has at least one sickle cell. As used herein, a "sickle cell" includes a cell which is an abnormal, crescent-shaped erythrocyte that contains sickle cell hemoglobin from a subject with sickle cell disease. "Sickling" includes the process whereby a normal-shaped cell becomes crescent-shaped.

As used herein, "administering" may be effected or performed using any of the methods known to one skilled in the art. The methods may comprise intralesional, intramuscular, subcutaneous, intravenous, intraperitoneal, liposome mediated, transmucosal, intestinal, topical, nasal, oral, anal, ocular or otic means of delivery.

As used herein, "effective amount" means an amount in sufficient quantities to accomplish the specific task, i.e., either treat the subject, reduce or prevent sickling of cells and/or reduce or prevent polymerization of hemoglobin. A person of ordinary skill in the art can perform simple titration experiments to determine what amount is required to treat the subject.

The amount of the antiviral agent will vary depending on the subject and upon the particular route of administration used. Based upon the antiviral agent, the amount can be delivered continuously, such as by continuous pump, or at periodic intervals. For example, on one or more separate occasions. Desired time intervals of multiple amounts of a particular antiviral agent can be determined without undue experimentation by one skilled in the art.

In one embodiment the effective amount of the compound comprises from about 1.0 ng/kg to about 100 mg/kg body weight of the subject. In another embodiment, the effective amount comprises from about 100 ng/kg to about 50 mg/kg body weight of the subject. In another embodiment, the effective amount comprises from about 1 $\mu$g/kg to about 10 mg/kg body weight of the subject. In a further embodiment, the effective amount comprises from about 100 $\mu$g/kg to about 1 mg/kg body weight of the subject. For example, amounts can range from 5 mg/kg to 10 mg/kg body weight of the subject administered intravenously; or 400 mg/kg to 800 mg/kg body weight of the subject administered orally; or 0.2 mg/ml to 0.4 mg/ml in vitro.

As used herein, "antiviral agent" includes a compound that inhibits the replication of viruses in cells, tissues, or organisms. Examples include but are not limited to Acyclovir (2-amino-1,9-dihydro-9-[(2-hydroxyethoxy)methyl]-6H-purin-6-one), Valacyclovir (L-valine, 2-[(2-amino-1,6-dihydro-6-oxo-9H-purin-9-yl)methoxy]ethyl ester, Pencyclovir (9-[4-hydroxy-3-(hydroxymethylbutyl)] guanine), Famcyclovir (2-[2-(amino-9H-purin-9-yl)]ethyl-1,3-propanediol diacetate), Ribavirin (1-beta-D-ribofuanosyl-1-H-1,2,4-triazol-3-carboxamide), Lamivudine ((2R,cis)-4-amino-1-(2-hydroxymethyl-1,3-oxathiolan-5-yl)-(1H)-pyrimidine-2-one), Amantadine (1-amantanamine hydrochloride), and Rimantadine ($\alpha$-methyltricyclo (3.3.1.1/3.7 decane-1-methylamine hydrochloride).

As used herein, "inhibits" means that the amount is reduced. In a preferred embodiment, inhibits means that the amount is reduced 100%.

This invention provides a method of inhibiting polymerization of hemoglobin which comprises contacting the hemoglobin with an amount of an antiviral agent effective to inhibit polymerization of the hemoglobin, so as to thereby inhibit polymerization of the hemoglobin.

As used herein, "polymerization" includes the process of forming a polymer from many monomeric units of hemoglobin. A polymer may be formed by any chemical bonding interaction between or among molecules, i.e. covalent, ionic, or van der Waals. As used herein, "aggregation" and "polymerization" may be used interchangeably.

In one embodiment of the above method, the hemoglobin is present in a cell and the contacting is effected by contacting the cell with the antiviral agent.

This invention provides a method of inhibiting sickling of a cell which comprises contacting the cell with an amount of an antiviral agent effective to inhibit polymerization of hemoglobin in the cell, so as to thereby inhibit sickling of the cell.

This invention provides a method of determining whether an antiviral agent is capable of treating a subject afflicted with sickle cell disease which comprises: (a) obtaining a suitable sample of cells from a subject afflicted with sickle cell disease; (b) subjecting the sample to conditions such that the cells in the sample sickle; and (c) comparing the amount of sickling of the cells in the presence of the antiviral agent with the amount of sickling of the cells in the absence of the antiviral agent, wherein an absence of sickling or a reduction in the amount of sickling in the cells in the presence of the antiviral agent compared with the amount of sickling of the cells in the absence of the antiviral agent indicates that the antiviral agent is capable of treating a subject afflicted with sickle cell disease.

This invention provides a method of determining whether an antiviral agent is capable of inhibiting sickling of a cell which comprises: (a) obtaining a suitable sample of cells from a subject afflicted with sickle cell disease; (b) subjecting the sample to conditions such that the cells in the sample sickle; and (c) comparing the amount of sickling of the cells in the presence of the antiviral agent with the amount of sickling of the cells in the absence of the antiviral agent, wherein an absence of sickling or a reduction in the amount of sickling in the cells in the presence of the antiviral agent compared with the amount of sickling of the cells in the absence of the antiviral agent indicates that the antiviral agent is capable of inhibiting sickling of the cell.

This invention provides a method of determining whether an antiviral agent is capable of inhibiting polymerization of hemoglobin which comprises: (a) obtaining a suitable sample of hemoglobin from a subject afflicted with sickle cell disease; (b) subjecting the sample to conditions such that the hemoglobin polymerizes; and (c) comparing the amount of turbidity of the sample in the presence of the antiviral agent with the amount of turbidity of the sample in the absence of the antiviral agent, wherein an absence or reduction in the amount of turbidity in the sample in the presence of the antiviral agent compared with the amount of turbidity in the sample in the absence of the antiviral agent indicates that the antiviral agent is capable of inhibiting polymerization of hemoglobin.

One skilled in the art would know under what conditions that hemoglobin polymerizes. One example is the condition wherein oxygen tension is reduced. Another example is the condition wherein the erythrocyte cell is contacted with a reducing agent. One of ordinary skill in the art will know what methods to use in order to reduce oxygen tension. A "reducing agent" includes an agent which is capable of removing oxygen bound to the heme group in hemoglobin. An example of a reducing agent is Sodium dithionite ($Na_2S_2O_4$).

One skilled in the art would know methods to use to compare the amount of sickling in samples. One example is a visual comparison. Such visual comparison may be done in several ways including but not limited to under a microscope and with the naked eye.

One skilled in the art would know methods to use to compare the turbidity in samples. One example is the use of a spectrophotometer. As used herein, "turbidity" includes the opacity caused by suspended particles or cells in a solution wherein a higher turbidity indicates that the sample has more polymerization or aggregation than a sample with lower turbidity.

In one embodiment of the above methods, the hemoglobin is Hemoglobin S. In another embodiment of the above methods, the hemoglobin is Hemoglobin SC.

In one embodiment of the above methods, the cell is an erythrocyte cell. As used herein, "erythrocyte cell" may be a red blood cell. In another embodiment of the above methods, the suitable sample is a sample of erythrocyte cells. In a further embodiment of the above methods, the cell is present in the subject and the contacting is effected by administering the antiviral agent to the subject.

In one embodiment of the above methods, the antiviral agent is a purine analog. In a further embodiment of the above methods, the purine analog is a guanosine analog. In one embodiment of the above method, the guanosine analog is acyclovir. In another embodiment of the above method, the guanosine analog is valacyclovir. As used herein, "purine analog" includes any compound which comprises a purine group. A "guanosine analog" includes any compound which comprises a guanosine group.

In one embodiment of the above methods, the sickle cell disease includes but is not limited to sickle cell anemia, sickle β-thalassemia, sickle cell-hemoglobin C disease and any other sickle hemoglobinopathy in which hemoglobin S interacts with a hemoglobin other than hemoglobin S. "Sickle hemoglobinopathy" is an abnormality of hemoglobin which results in sickle cell disease or sickle variants.

In one embodiment of the above methods, the subject is a mouse, rat, dog, guinea pig, ferret, rabbit, primate, or human being. As used herein, "subject" means any animal or artificially modified animal capable of being afflicted with sickle cell disease. In the preferred embodiment, the subject is a human being.

The routes of administration include but are not limited to intralesional, intramuscular, subcutaneous, intravenous, intraperitoneal, liposome mediated, transmucosal, intestinal, topical, nasal, oral, anal, ocular and otic delivery.

This invention will be better understood from the Experimental Details that follow. However, one skilled in the art will readily appreciate that the specific methods and results discussed are merely illustrative of the invention as described more fully in the claims which follow thereafter.

EXPERIMENTAL DETAILS

A. Materials and Methods

Solutions of acyclovir were prepared from "Acyclovir for Injection" (ESI Lederle, Philadelphia, Pa.) by first dissolving 500 mg in 2.5 ml distilled water. This solution of 200 mg/ml is stored in the refrigerator. Before use, it is warmed to 37° C. to maintain a clear solution. An aliquot is diluted 40-fold in distilled water and the various solutions used in the experiments prepared in PBS.

Using methodologies modeled after those previously developed in other laboratories, assays to measure in vitro aggregation of a solution of hemoglobin S ("HbS") (13, 14) and in vitro sickling of intact HbS cells (15) were carried out as follows.

Inhibition of Aggregation of Hemoglobin S

To a 10 mm cuvette (Type 9GL14S, Septum seal, Uvonic Instruments, Plainview, N.Y. 11803) containing 0.9 ml of 1.8M phosphate buffer, pH 9.4, was added 5 mg of $Na_2S_2O_3$. The cuvette was capped and two #25 hypodermic needles were inserted through the soft plastic seals. Nitrogen was passed over the surface of the solution for 15 minutes to drive off oxygen; the cuvette was then gently shaken to dissolve the $Na_2S_2O_3$. The cuvette was then placed in an ice bath to bring the solution to 4° C. and 0.1 ml of a 2 g/dl HbS solution (13, 14) was added through the plastic diaphragm with a Hamilton air-tight syringe. The temperature of the solution in the cuvette was raised by placing it in a 30° C. bath and then into a spectrophotometer in which the increase in turbidity was measured with time at 700 nm. A control curve was obtained after which the course of turbidity was measured in the presence of the various reagents including acyclovir (Lederle, for injection; dilutions were in PBS) and valacyclovir. The latter was extracted with phosphate buffer from tablets of Valtrex (Glaxo Wellcome).

Inhibition of Sickling of Intact Erythrocytes by Acyclovir

The procedure used was essentially that of Cerami and Manning (15). The source of the red cells was human blood in which HbS represented essentially 100% of the total hemoglobin as determined by electrophoresis on a cellulose acetate membrane in a Supre-Heme® Tris-EDTA-boric acid buffer (Helena Laboratories, Beaumont, Tex.).

Ten microliters of blood was diluted to 5 ml with PBS and 1 ml aliquots were distributed into the same type of cuvettes used to study hemoglobin S aggregation (see above). Two #25 hypodermic needles were inserted into each plastic diaphragm and nitrogen was passed over the surface of the erythrocyte suspension for 15 minutes with periodic gentle shaking. The hypodermic needles were removed and the sealed cuvettes were left for 2 hours at room temperature. The control cuvette was treated identically except that the cap was loosened for the 2 hour period.

Then 250 $\mu$l of 10% buffered formalin (Metpath) was added to the cell suspensions, which were allowed to stand at room temperature for 15 minutes. The cell suspensions were then sedimented by centrifugation, suspended in 100 $\mu$l of PBS and examined under the microscope.

B. Results

Inhibition of Aggregation of Hemoglobin S at Low Oxygen Tension

Figure 3:
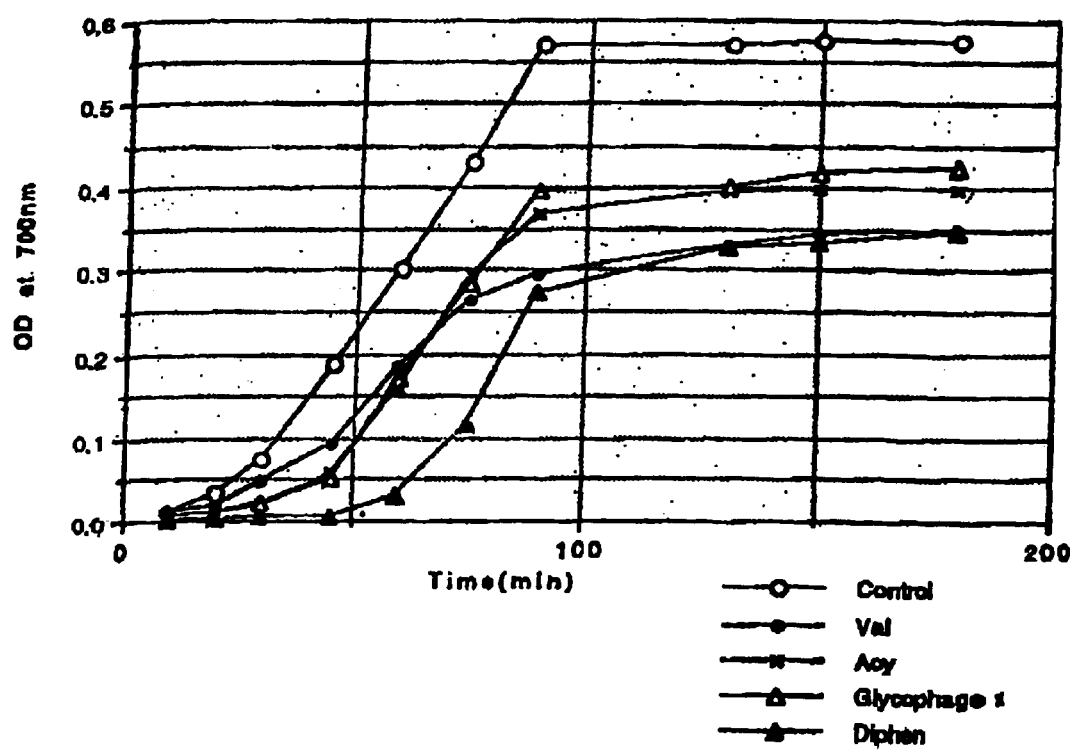

Aggregation of soluble HbS occurred in response to lowering of oxygen tension (control, FIG. 1 and FIG. 3) as did inhibition by hemoglobin A (not shown). Two antiviral agents, acyclovir and valacyclovir, were identified as inhibiting in vitro aggregation of HbS in a similar fashion. The results for acyclovir are shown in FIG. 1. The results for both acyclovir and valacyclovir are shown in FIG. 3.

Inhibition of Erythrocyte Sickling

Figure 2A:
Figure 2B:
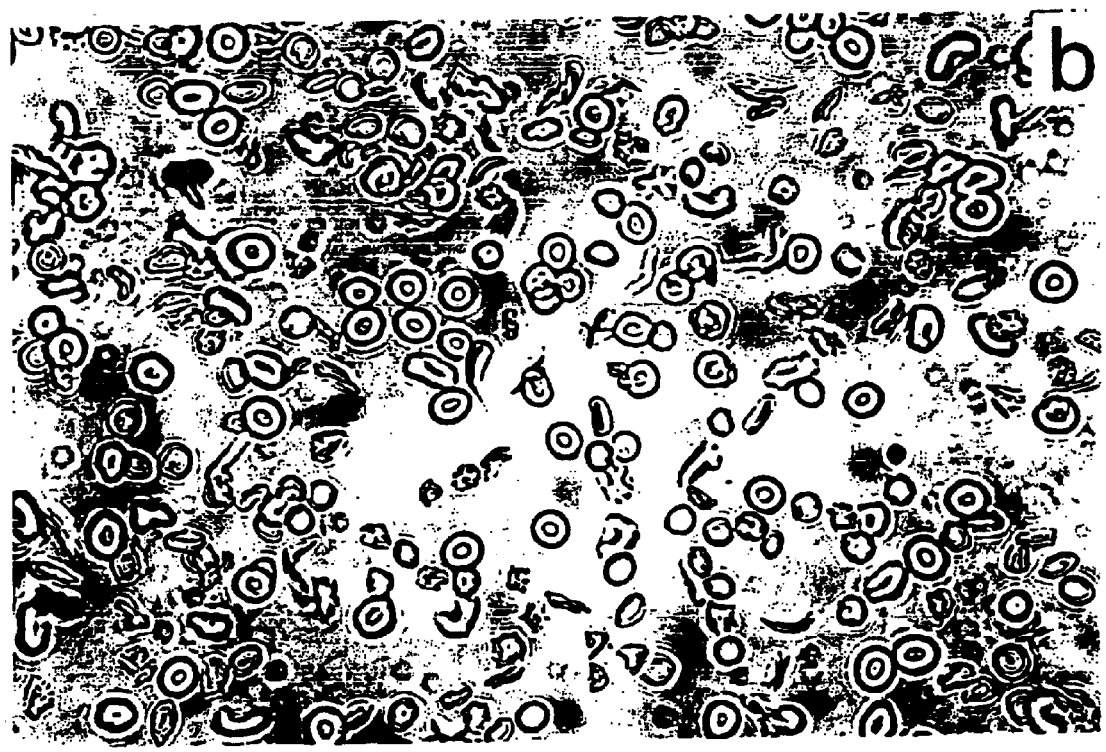
Figure 2C:
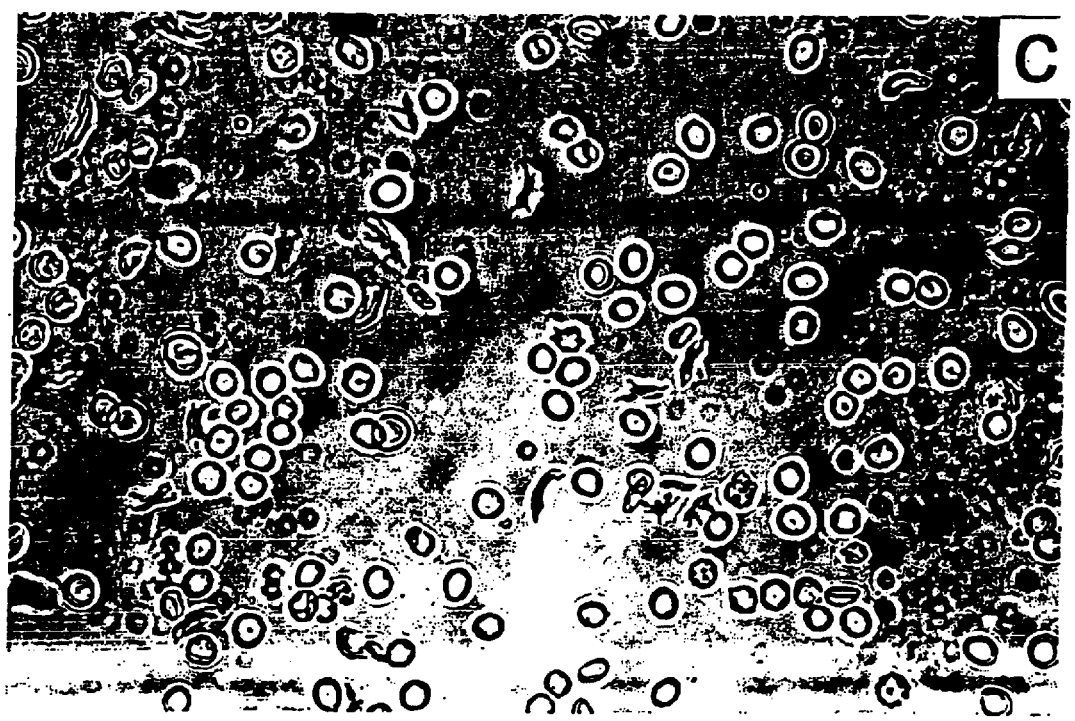
Figure 2D:
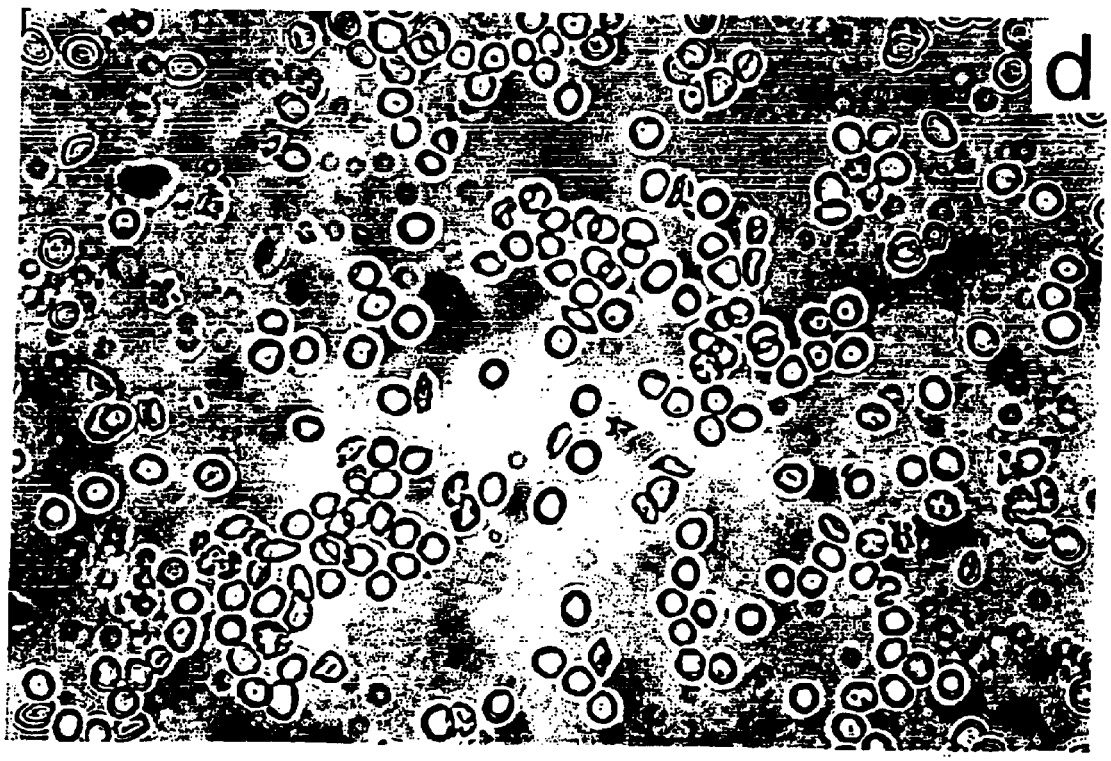
Figure 2E:
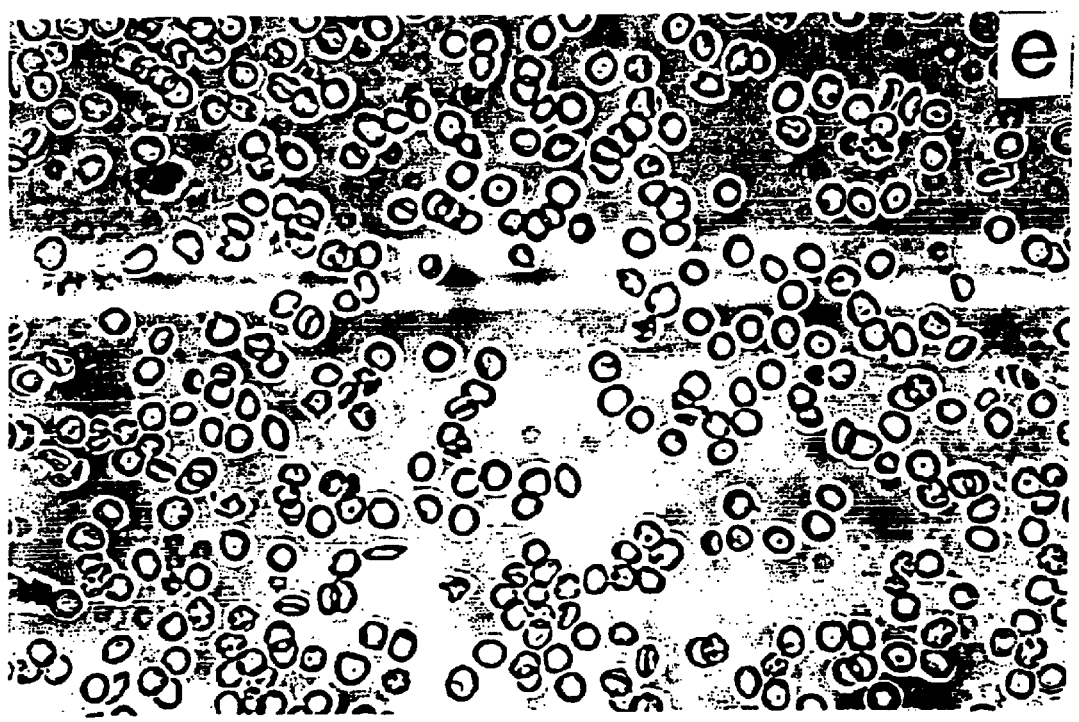

Erythrocytes were taken from an individual in whom 95+% of total hemoglobin was HbS. The erythrocytes were placed under low oxygen tension in the absence or presence of a acyclovir at concentrations of 0.2, 0.3 and 0.4 mg/ml. The erythrocytes were then formalin-fixed and examined under a microscope. In FIG. 2A (the control), extensive sickling is apparent. Minimal sickling occurred at acyclovir concentrations of 0.2 mg/ml (FIG. 2B) and 0.3 mg/ml (FIG. 2C); essentially no sickling is seen in the presence of 0.4 mg/ml acyclovir (FIG. 2D). FIG. 2E represents erythrocytes from the same patient under aerobic conditions. Similar results were obtained with valacyclovir.

C. Discussion

In a screen of many therapeutic agents for their ability to inhibit aggregation of HbS, acyclovir and valacyclovir were found to be effective. They were active at relatively low concentrations compared, for example, with KCNO (15, 16) in which a concentration of 2.4 mg/ml was used, i.e. more than 10× the effective concentration of acyclovir (FIG. 2). Moreover, there is experimental evidence that acyclovir is actively transported into erythrocytes via a nucleobase transporter rather than by a concentration-dependent simple diffusion (17).

It is also worth noting that the erythrocyte sickling experiments (FIG. 2) were carried out essentially in the absence of oxygen. Clinically, sickling occurs under milder hypoxic conditions with oxygen tensions as high as 45 mm (18). And it has been reported that recurrence of symptoms of sickle cell disease can be prevented by keeping the proportion of sickling cells at levels as high as 60% by transfusion (19). We are well below 60% sickling at our lowest acyclovir concentration (FIG. 2B). There is a good possibility, therefore, that even lower concentrations of acyclovir will be effective in preventing sickle cell crises. Finally, acyclovir caused no significant change in oxygen affinity or Hill coefficient in experiments with human hemoglobin (J. E. Knapp and W. E Royer, Jr., personal communication).

REFERENCES

1. Steinberg, M. H. (1999), "Management Of Sickle Cell Disease", *N. Engl. J. Med.* 340: 1021–1030.
2. Pauling, L., H. A. Itano, S. J. Sinpur, I. C. Wells (1945), "Sickle Cell Anemia, A Molecular Disease", *Science* 110: 543–545.
3. Bunn, H. F. (1997), "Pathogenesis And Treatment Of Sickle Cell Disease", *N. Engl. J. Med.* 337: 762–769.
4. Dover, G. J., R. K. Humphries, J. G. Moore, T. J. Ley, N. S. Young, S. Charache, A. W. Nienhuis (1986), "Hydroxyurea Induction Of Hemoglobin F Production In Sickle Cell Disease; Relationship Between Cytotoxicity And F Cell Production", *Blood* 67: 735–738.
5. Charache, S., G. J. Dover, M. A. Moyer, J. W. Moore (1987), "Hydroxyurea-induced Augmentation Of Fetal Hemoglobin Production In Patient With Sickle Cell Anemia", *Blood* 69: 109–116.
6. Ballas, S. K., G. J. Dover, S. Charache (1989), "Effect Of Hydroxyurea On The Rheological Properties Of Sickle Erythrocytes In Vivo", *Am. J. Hemotol.* 32: 104–111.
7. Rogers, G. P., G. J. Dover, C. T. Noguchi, A. N. Schecter, A. W. Nienbuis (1990), "Hematologic Responses Of Patients With Sickle Cell Disease To Treatment With Hydroxyurea", *N. Engl. J. Med.* 322: 1037–1045.
8. Goldberg, M. A., C. Brugnara, G. J. Dover, L. Shapira, S. Charache, H. F. Bunn (1990), "Treatment Of Sickle Cell Anemia With Hydroxyurea And Erythropoietin", *N. Engl. J. Med.* 323: 366–372.
9. Orringer, E. P., D. S. Blythe, A. E. Johnson, G. Phillips, Jr., G. J. Dover, J. C. Park (1991), "Effects Of Hydroxyurea On Hemoglobin F And Water Content In The Red Blood Cells Of Dogs And Patients With Sickle Cell Anemia", *Blood* 78: 212–216.
10. Charache, S., M. C. Terrin, R. D. Moore, G. J. Dover, F. B. Barton, S. V. Eckert, R. P. McMahon, D. R. Bonds (1995), "Effect Of Hydroxyurea On The Frequency Of Painful Crises In Sickle Cell Anemia", *N. Engl. J. Med.* 332: 1317–1322.
11. Charache, S., F. B. Barton, R. D. Moore, M. L. Terrin, M. H. Steinberg, G. J. Dover, S. K. Ballas, R. P. McMahon, O. Castro, E. P. Orringer (1996), "Hydroxyurea And Sickle Cell Anemia: Clinical Utility Of A Myelosuppressive 'Switching' Agent: The Multicenter Study of Hydroxyurea In Sickle Cell Anemia", *Medicine* (Baltimore) 75: 300–326.
12. Ferster, A., C. Vermylen, G. Cornu, M. Buyse, F. Corazza, C. Devalck, P. Fondu, M. Toppet, E. Sariban (1996), "Hydroxyurea For Treatment Of Severe Sickle Cell Anemia: A Pediatric Clinical Trial", *Blood* 88: 1960–1964.
13. Huisman, T. H. J. and A. M. Dozy (1965), "Studies On The Heterogeneity Of Hemoglobin. IX. The Use Of Tris (hydroxymethyl) aminomethane.HCI In The Ion Exchange Chromatography Of Hemoglobins", *J. Chromatog.* 19: 160–169.
14. Adachi, K., M. Ozgue, T. Asakura (1980), "Nucleation-Controlled Aggregation Of Deoxyhemoglobin S Participation Of Hemoglobin A In The Aggregation Of Hemoglobin S In Concentrated Phosphate Buffer", *J. Biol. Chem.* 255: 3092–3099.
15. Cerami, A., and J. M. Manning (1971), "Potassium Cyanate As An Inhibitor Of The Sickling Of Erythrocytes In Vitro", *Proc. Natl. Acad. Sci. USA* 68: 1180–1183.
16. Gillette, P. N., C. M. Peterson, S. L. Yang, A. Cerami (1974), "Sodium Cyanate As A Potential Treatment For Sickle Cell Disease", *N. Eng. J. Med.* 290: 654–660.
17. Mahony, W. B., B. A. Domin, R. T. McConnell, T. P. Zimmerman (1998), "Acyclovir Transport Into Human Erythrocytes" *J. Biol. Chem.* 263: 9285–9291.
18. Hahn, E. V., and E. B. Gillespie (1927), "Sickle Cell Anemia: Report Of A Case Greatly Improved By Splenectomy: Experimental Studies Of Sickle Cell Formation", *Arch. Intern. Med.* 39: 233–254.
19. Charache, S., and C. L. Conley (1964), "Rate Of Sickling Of Red Cells During Deoxygenation Of Blood From Persons With Various Sickling Disorders", *Blood* 24: 25–48.

What is claimd is:

1. A method of treating a subject afflicted with sickle cell disease which comprises administering to the subject an amount of an antiviral agent, wherein the antiviral agent is valacyclovir, pencyclovir, or famcyclovir, effective to inhibit sickling of a cell in the subject, so as to thereby treat the subject.

2. The method of claim 1, wherein the cell is an erythrocyte cell.

3. The method of claim 1, wherein the sickle cell disease is selected from the group consisting of sickle cell anemia, sickle β-thalassemia, sickle cell-hemoglobin C disease and any other sickle hemoglobinopathy in which hemoglobin S interacts with a hemoglobin other than hemoglobin S.

4. The method of claim 1, wherein the subject is a mouse, rat, dog, guinea pig, ferret, rabbit, primate, or human being.

5. The method of claim 1, wherein the antiviral agent is administered to a subject via intralesional, intramuscular, subcutaneous, intraperitoneal, liposome mediated, transmucosal, intestinal, topical, nasal, oral, anal, ocular or otic delivery.

* * * * *